United States Patent [19]
Loertscher

[11] Patent Number: 5,222,952
[45] Date of Patent: Jun. 29, 1993

[54] METHOD FOR LASER SCLEROSTOMY

[76] Inventor: Hanspeter Loertscher, Zedtwitzweg 2, CH-3626, Hunibach, Switzerland

[21] Appl. No.: 904,215

[22] Filed: Jun. 25, 1992

Related U.S. Application Data

[63] Continuation-in-part of Ser. No. 675,442, Mar. 26, 1991, Pat. No. 5,151,098, which is a continuation-in-part of Ser. No. 556,900, Jul. 23, 1990, abandoned, which is a continuation-in-part of Ser. No. 264,438, Oct. 28, 1988, Pat. No. 4,963,142.

[51] Int. Cl.⁵ .............................................. A61B 17/32
[52] U.S. Cl. ......................................... 606/6; 606/15
[58] Field of Search ........................................ 606/3-6, 606/13-16; 128/395-398

[56] References Cited

U.S. PATENT DOCUMENTS

| 4,122,853 | 10/1978 | Smith | 606/19 |
| 4,385,832 | 5/1983 | Doi et al. | 606/16 |
| 4,819,632 | 4/1989 | Davies | 606/15 |
| 4,846,172 | 7/1989 | Berlin | 128/395 |
| 4,865,029 | 9/1989 | Pankratov et al. | 606/4 |
| 4,878,492 | 11/1989 | Sinofsky et al. | 606/13 |
| 5,129,895 | 7/1992 | Vassiliadis et al. | 606/6 |

Primary Examiner—Max Hindenburg
Attorney, Agent, or Firm—Hopkins & Thomas

[57] ABSTRACT

A method for performing endolaser microsurgery on ocular and like tissues utilizing a laser delivery system and an intraocular probe for delivering the laser energy to the tissues comprising the steps of forming an incision in the conjunctiva surrounding the sclera, introducing the probe through the incision, moving the probe anteriorly beneath the conjunctiva to a site remote from the initial incision, and ablating by laser a drainage fistula through the sclera for relieving intraocular pressure.

12 Claims, 3 Drawing Sheets

METHOD FOR LASER SCLEROSTOMY

This application is a continuation-in-part of application Ser. No. 07/675,442 filed Mar. 26, 1991, now U.S. Pat. No. 5,151,098 which is a continuation-in-part of application Ser. No. 07/556,900 filed July 23, 1990, now abandoned, which is a continuation-in-part of application Ser. No. 07/264,438 filed Oct. 28, 1988, now U.S. Pat. No. 4,963,142.

BACKGROUND OF THE INVENTION

Recent advances in technology and techniques have made the use of lasers in surgical procedures increasingly common. The precision attained through the use of lasers and laser equipment has particular advantages in microsurgical procedures which were formerly not possible using conventional instruments. As the field has developed, however, some of the techniques which are now in use and which are theoretically sound have led to previously unforeseen problems.

As an example, the conventional surgical procedure to produce a new outflow path for the aqueous humor in glaucoma patients has consisted of several steps, making the operation complicated and relatively traumatic. As a result, the procedure often fails due to wound healing, which closes the newly formed opening by scarring. Several authors have thus investigated the use of lasers to simplify this procedure and to reduce trauma:

Q-switched YAG laser pulses have been delivered by means of a specially designed mirror-contact lens across the anterior chamber and aimed at the sclera anteriorly to the trabeculum meshwork. The difficulties and uncertainties of this method are: (1) The high energies (50 mj and more) per pulse cause hemorrhages of the iris due to the shock waves. Consequently, the iris base is preoperatively photocoagulated. (2) Special precautions are necessary to not inadvertently penetrate the conjunctiva. The energy per pulse can be reduced by injecting silver oxide intralimbally, which complicates the procedure.

CW-YAG laser was delivered through a sapphire contact probe, which was inserted through the cornea opposite to the area of trabecular meshwork to be perforated, the tissue touched by the sapphire tip was vaporized. There are essentially two difficulties anticipated:

(1) Inserting the sapphire tip is a invasive procedure and;

(2) using a cw: YAG laser causes more thermal damage to remaining tissue than by using short pulsed lasers, thus increasing wound healing reactions and lowering the success rate.

CW ultraviolet laser had been delivered through an optical fiber in a similar way as the sapphire tip described above. The anticipated problems are the same.

308 nm wavelength pulses from an excimer laser had been delivered through an optical fiber the same way as above. Beside the same disadvantage of being an invasive procedure, this wavelength causes high risks because of its phototoxic effects to retina and lens, and because of potential carcinogenic effects.

A 193 nm excimer had been used ab externo after removal of the conjunctiva. This wavelength cannot be transmitted through an optical fiber.

SUMMARY OF THE INVENTION

It is, therefore, one of the principal objects of the present invention to provide a method for performing endolaser microsurgery which is particularly applicable to glaucoma patients for relieving intraocular pressure.

Another object of the present invention is to provide an apparatus for performing microsurgery that is used in conjunction with a suitable laser delivery system for ablating tissue and aspirating the ablated tissue and/or fluids using the same instrument.

A further object of the present invention is to provide an intraocular probe for use in microsurgery that provides safe and effective delivery of the laser energy to a very limited and specific area.

A still further object of the present invention is to provide a means of coupling the laser energy delivery system to the intraocular probe/aspiration means.

These and additional objects are attained by the present invention which relates to an intraocular probe capable of delivering pulses of laser energy to a specifically defined area to form, for example, a drainage fistula through the sclera in cases of otherwise poorly controlled glaucoma. The probe contemplated by the present invention is coupled to a suitable laser delivery system and includes a passageway integrally formed therewith for aspiration of ablated tissue and/or fluids.

The method contemplated by the present invention involves the formation of an incision at a site remote from the drainage fistula so as to minimize or eliminate completely the possibility of the fistula being closed by the healing of the original incision in the case of a sclerostomy. The probe is substantially rigid and is manipulated either manually or mechanically to the appropriate site for the tissue ablation.

Various additional objects and advantages of the present invention will become apparent from the following description, with reference to the accompanying drawings.

DETAILED DESCRIPTION OF THE PREFERRED EMBODIMENT

Figure 1A:
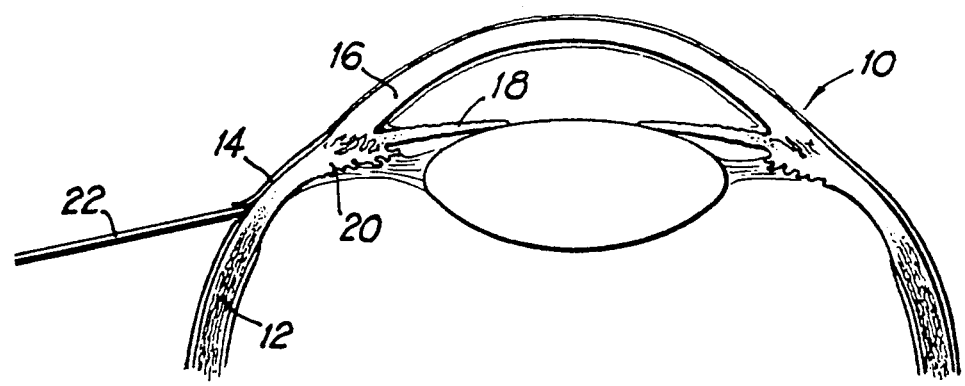
FIG. 1A is partial cross-sectional view of a human eye, illustrating the initial incision.

Referring now more specifically to the drawings, and to FIG. 1 in particular, numeral 10 indicates generally a human eye, shown in partial cross-section. The portions of the eye relative to the present invention are illustrated and include the sclera 12, the conjunctiva 14, the cornea 16, the iris 18, and the ciliary body 20.

Figure 1B:
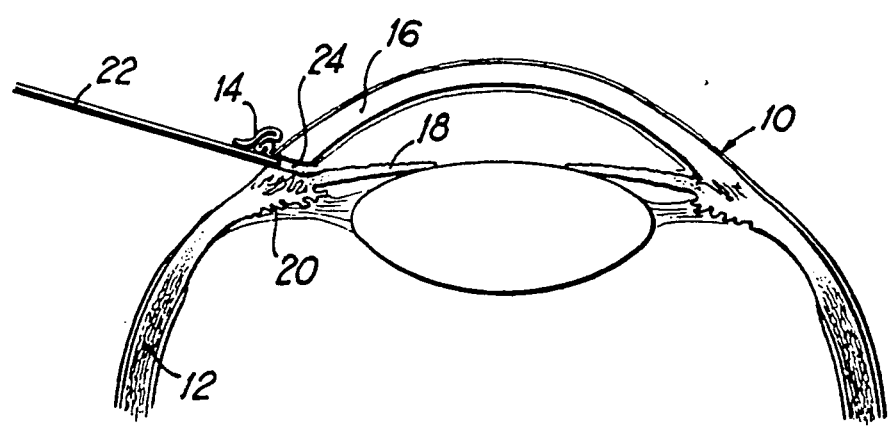
FIG. 1B is a partial cross-sectional view similar to the preceding figure, illustrating the formation of the drainage fistula.
Figure 1C:
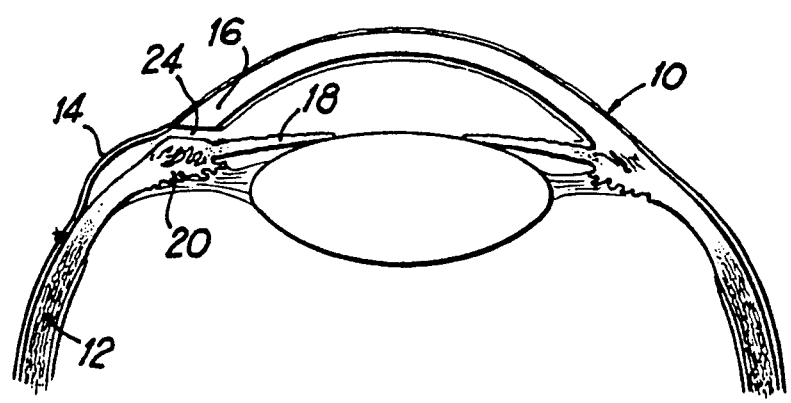
FIG. 1C is a partial cross-sectional view similar to the preceding figures, illustrating the completed procedure.

FIGS. 1A, 1B and 1C illustrate the present inventive method for a sclerostomy procedure. An intraocular probe 22, which is coupled to a laser delivery system (not shown) is used to ablate a small incision in the conjunctiva 14 at a site remote from the site of the drainage fistula to be formed. The rigid probe is moved anteriorly which causes the elastic conjunctiva to be displaced, as shown in FIG. 1B. Pulses of laser energy from, for example, a Holmium laser (2.1 micron wavelength, penetration in water 300 microns), an Erbium laser (wavelength 2.94 microns, penetration in water 1 micron) or a similar laser system, are delivered through the probe to ablate the corneal tissue and form a drainage fistula 24 through which the aqueous humor can pass for relieving intraocular pressure.

Upon removal of the probe, the conjunctiva is replaced and sutured at the point of incision, as shown in FIG. 1C. A major advantage of the present method is the formation of the drainage fistula 24 at a site remote from the site of the incision. Any scarring which may occur at the site of the incision, which could possibly block the fistula if the operation were performed at a single site, is avoided with the present technique. The method will be further detailed along with the description of the probe hereinafter.

Vitrectomy is a fundamental importance in the treatment of vitroretinal diseases. The removal of the gel-like vitreous and associated membranes is a difficult and delicate procedure, particularly when strands attached to the retina are present. Various mechanical instruments have been devised for cutting vitreous and removing fragments. The inherent disadvantage of such devices is the traction exerted on adjacent structures when vitreous and especially bands are sheared, as any mechanical disturbance of such strands will tear the retina.

The use of $CO_2$ lasers had been investigated mainly because its tissue vaporizing effects avoid traction on the retina. The laser beam is delivered through an articulated arm or special optical fibers into an intraocular probe, consisting basically of a hollow metal tube (typically 1 mm diameter) closed by an infrared transmitting window. The disadvantages with the $CO_2$ laser consisted in either a slow cutting rate resulting in a rather lengthy procedure, or in causing remote damage to surrounding tissues, such as the retina. The remote damages consisted of coagulations due to head diffusion, steam formation and convection of heated and liquified vitreous.

The present invention suggests the use of pulsed lasers, the pulse widths of which are smaller than the specific thermal relaxation time, and the wavelength of which is highly absorbed by water. As previously suggested by Wolbarsht, and experimentally shown by others, such laser pulses are able to ablate thin layers of tissue (in the order of up to 10 micron depth) with minimal damage to the remaining tissue. Because of the high absorption and small penetration depth, the volume of the evaporated or ablated mass per pulse is relatively limited. This invention therefore proposes the use of an intraocular probe, which is able to deliver the laser beam to an area of tissue which is significantly larger than the area of the optical fiber able to transmit that laser pulse, and which allows the aspiration of the ablated material, and in which the diameter of the probe does not exceed approximately 1.0 mm to 1.5 mm.

Figure 2:
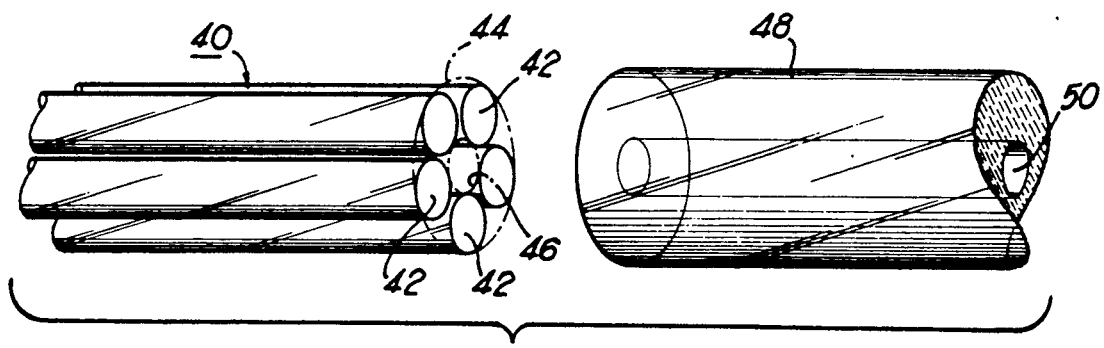
FIG. 2 is a partial perspective and side elevational view of one embodiment of the coupling of the laser delivery means and the intraocular probe.

Detailed views of the operative portions of the intraocular probe and several embodiments thereof are illustrated in FIGS. 2 through 8A. FIG. 2 illustrates a laser delivery means 40 comprising a bundle of optical fibers 42 contained within a suitable housing 44. A central passageway 46 is maintained for aspiration of ablated material. The fibers are coupled to a suitable laser delivery system (not shown) in a conventional manner. The delivery means 40 in FIG. 2 is coupled through suitable means (not shown) to a tubular member 48, preferentially of sapphire, which also contains a central passageway 50, which is coaxially aligned with passageway 46. Sapphire is the preferred material for the tube due to its superior laser transmission properties, high mechanical strength, and high melting point, although other suitable materials having like qualities may be used.

Figure 3:
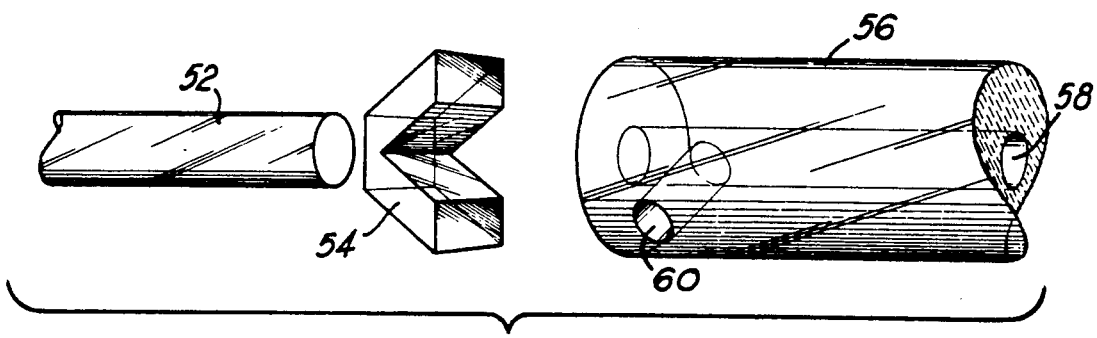
FIG. 3 is a partial perspective and side elevational view of an alternate embodiment of coupling the laser delivery means to the intraocular probe.
Figure 4:
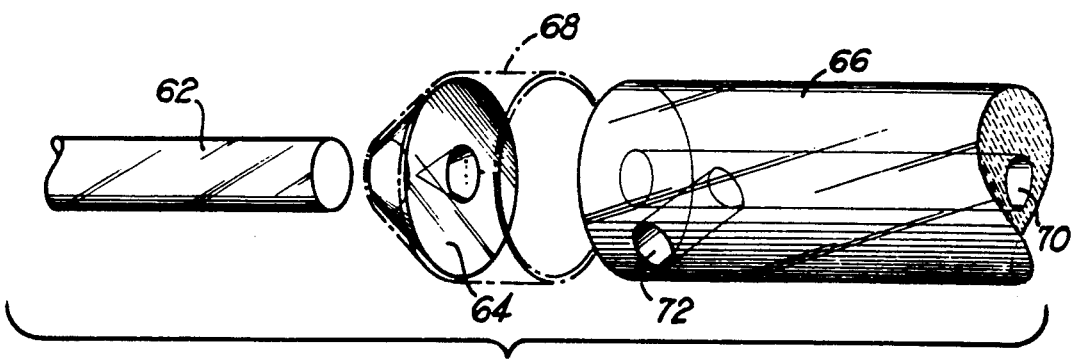
FIG. 4 is a partial perspective and side elevational view of another embodiment of the coupling of the laser delivery means to the intraocular probe.
Figure 5:
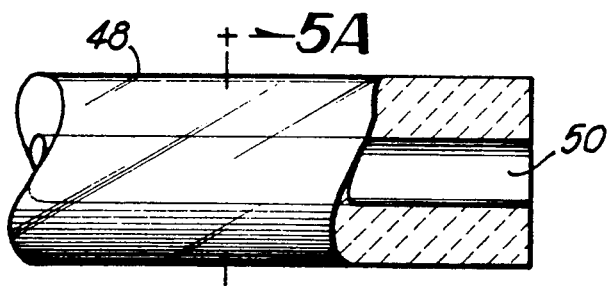
FIG. 5 is a partial cross-sectional and side elevational view of one embodiment of the intraocular probe.
Figure 5A:
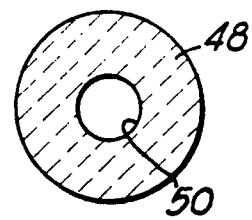
FIG. 5A is a cross-sectional view, taken on line 5A—5A of FIG. 5.

FIGS. 3 and 4 illustrate alternate embodiments of delivering the laser energy to the sapphire tube. In FIG. 3, a single optical fiber 52 delivers the laser energy to a sapphire prism (which is shown in perspective view for clarity) which splits the beam into two or more components for transmission into the sapphire tube 56. Coupling of the prism to the tube 56 is accomplished in any suitable manner, such as with a high temperature adhesive or a suitable tubular sleeve (not shown). Tube 56 also contains a central passageway 58 for aspiration of ablated material and may also include a secondary, offset passageway 60 for irrigation and/or aspiration purposes A third embodiment, shown in FIG. 4, couples the optical fiber 62 to a sapphire cone 64, which diverts the laser energy to the sapphire tube 66. A suitable connecting sleeve 68, or similar means couples the cone 64 to the tube 66. A central aspiration passageway 70 is provided through tube 66 along with a secondary offset passageway 72 which communicates with passageway 70 similar to that shown in FIG. 3.

A central theme of the present application is the use of an intraocular probe, typically comprising a relatively thick-walled tube of approximately 15 to 30 millimeters in length and a diameter of approximately 1 millimeter. Certain required characteristics for the probe include:

a) mechanical rigidity, so that it does not break or fracture upon its manipulations inside the eye or other organ;

c) the probe is unaffected by the laser interaction with the tissue; and d) the aspiration of evaporated or ablated tissue through a central passageway.

Thus, the intraocular probe is typically a hollow tube comprised of an optical material able to transmit laser wavelengths which are highly absorbed by water the cylindrical tube wall has sufficient thickness to transmit sufficient laser energy to ablate the tissue. The central cylindrical passageway has sufficient diameter to aspirate evaporated or ablated material or fragments thereof. A suitable aspiration system, known in the art, is connected to the central passageway or secondary passageway in any suitable manner.

For certain applications, depending on the laser delivery system utilized, specialized probe design is required. When combined with a Holmium laser (2.1 micron wavelength, penetration in water 300 microns) the laser light is reflected from the inner and outer surfaces of the tube by total reflection, thus the probe can be that illustrated in FIGS. 2 through 5.

With the use of the Erbium laser (2.94 micron wavelength, penetration in water 1 micron), the tube's walls must be protected from contact with water or any water containing material by a special reflective coating or a cladding, or by additional metal tubes with an airspace between the tube and the core such specialized probes are illustrated in FIGS. 6 through 8A.

Figure 6:
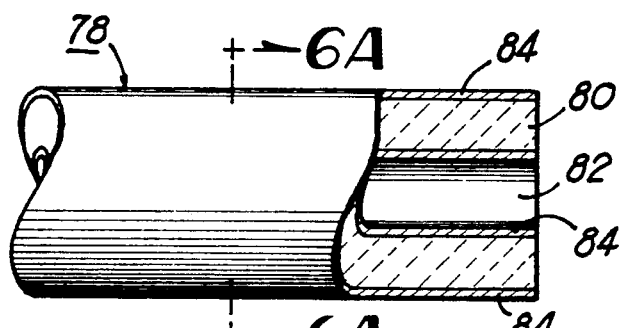
FIG. 6 is a partial cross-sectional and side elevational view of another embodiment of the probe.
Figure 6A:
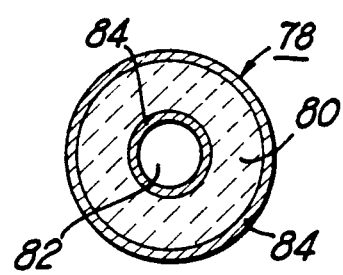
FIG. 6A is a cross-sectional view taken on line 6A—6A of FIG. 6.

FIGS. 6 and 6A illustrate an embodiment of a probe 78 with a sapphire tube 80 having a central passageway 82 in which the tube 80 and passageway 82 are surrounded by a reflective coating or a cladding material 84 having a low index of refraction.

Figure 7:
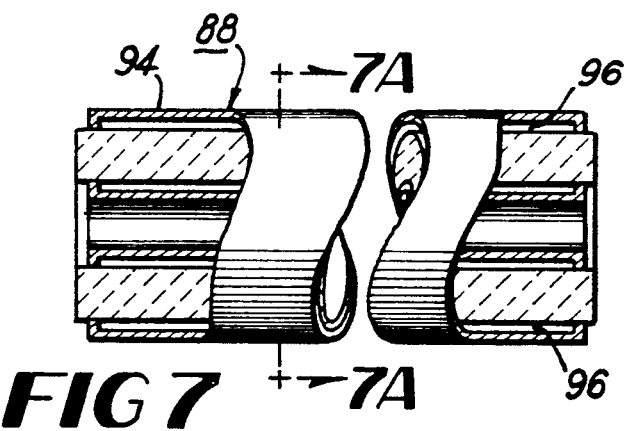
FIG. 7 is a partial cross-sectional and fragmentary side elevational view of another embodiment of the probe.
Figure 7A:
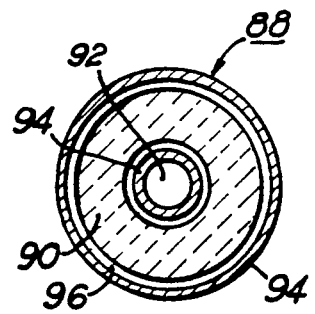
FIG. 7A is a cross-sectional view taken on line 7A—7A of FIG. 7.

FIGS. 7 and 7A illustrate an embodiment of a probe 88 having a sapphire tube 90 with a central passageway 92. The sapphire tube 90 and the central passageway 92 are surrounded by a suitable metallic tube 94 with an airspace or void 96 therebetween, for total reflection of the beam.

Figure 8:
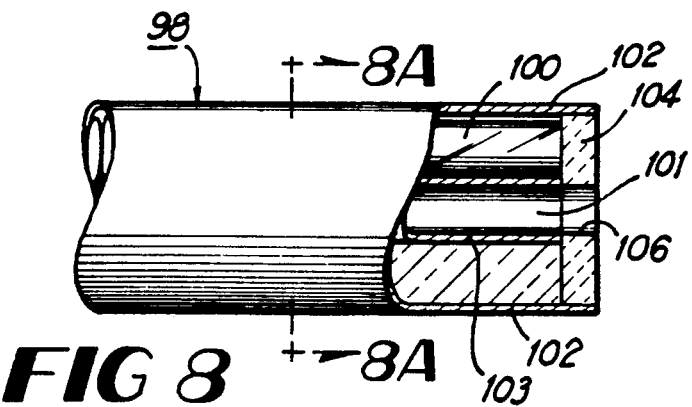
FIG. 8 is a partial cross-sectional and side elevational view of another embodiment of the probe.
Figure 8A:
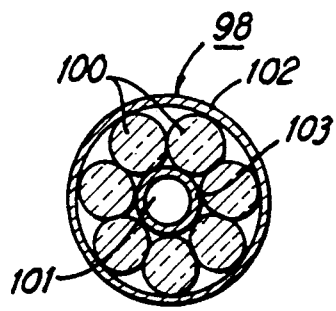
FIG. 8A is a cross-sectional view taken on line 8A—8A of FIG. 8.

FIGS. 8 and 8A illustrate other modification wherein the probe 98, comprised of a bundle of optical fibers 100 with a central passageway 101, all are contained within or between two coaxial tubes 102 and 103 which can be metallic tubes sapphire tubes, or other suitable material. The probe 98 contains a sapphire window 104 for transmission of the laser light and for sealing the distal end of the probe, the window having a central aspiration passageway 106.

Since the laser wavelengths used have only a relatively small penetration depth of a few microns in most ocular tissues, only thin layers can be ablated per laser pulse. By delivering the laser beam through an annular surface, as described hereinabove, which is approximately an order of magnitude larger than the end surface or diameter of the optical fibers used, an increased volume of tissue can be ablated per pulse. This, when combined with an aspiration canal in a probe of a minimal outer diameter, provides the laser delivery system to be utilized more safely and efficiently than has previously been accomplished.

The invention is also useful in other surgical areas, for example, as a substitute for ultrasonic phacoemulsification in cataract surgery, in vitreous surgery, in lithotripsy (removal of gallstones and kidney stones) and in the sclerostomy procedure described hereinabove.

Thus, the invention contemplates the following:

Wavelengths which are highly absorbed by the sclera, so that the penetration depth is smaller than typically 1 mm. The two wavelength regions are 1.4 to 10 micron, and below 200 nm.

Pulse durations short enough to not cause significant thermal damage to the remaining scleral tissue, and thus reducing the risk of fistula closure.

Delivering such pulses through an optical fiber, the end of which is brought in direct contact with the corneoscleral tissue.

Delivering such pulses through an optical fiber, the end of which is introduced into a metal tube, the end of the metal tube being sealed with sapphire window or any other material transmitting sufficient laser energy, and with the window brought in contact with the corneoscleral tissue to be penetrated.

Delivering such pulses through an articulated arm, at the end of which the beam is focused into a metal tube, the end of the metal tube being sealed with a beam transmitting window, which is brought in contact with the tissue to be perforated.

The probe (metal tube with window, or bare fiber) can be used ab interna, by inserting the probe through the cornea opposite to the area of the corneoscleral tissue to be perforated.

Possible lasers to be used are: Erbium: YAG laser at 2.94 micron, Holmium: YAG or Holmium: YSGG at 2.1 micron, and argon fluoride excimer laser at 193 nm. At 2.94 micron, Zirconium fluoride fibers can be used to transmit this wavelength, whereas at 2.1 micron, silica fibers can be used.

Thus, while an embodiment and modifications thereof of an apparatus, intraocular probe, and method of endolaser microsurgery have been disclosed, illustrated, and described in detail herein, various additional changes and modifications may be made without departing from the scope of the present invention.

I claim:

1. A method for performing endolaser microsurgery on ocular and like tissues utilizing a laser delivery system and an intraocular probe for delivering the laser energy to the tissues comprising the steps of forming an incision in the conjunctiva surrounding the sclera, advancing the probe through the incision, moving the probe anteriorly beneath the conjunctiva to a site remote from the initial incision, and ablating by laser a drainage fistula through the sclera for relieving intraocular pressure.

2. The method of claim 1 in which said initial incision is formed by the application of pulsed laser energy through said probe.

3. The method of claim 1 in which said initial incision in the conjunctiva is at a site remote from the sclerostomy or sclerostomy site.

4. The method of claim 1 and including the additional step of aspirating the ablated tissue through said probe.

5. The method of claim 3 in which said re-securing step includes suturing the displaced conjunctiva at the site of said incision.

6. A method for performing endolaser microsurgery on ocular and like tissue utilizing a laser delivery system and an intraocular probe for delivering the laser energy to the tissues comprising the steps of forming an incision in the conjunctiva surrounding the sclera, introducing and advancing the probe through the incision, moving the probe anteriorly beneath the conjunctiva to a site remote from the initial incision, and ablating by laser a drainage fistula through the sclera for relieving intraocular pressure, said initial incision in the conjunctive being made at a site remote from the sclerostomy or sclerostomy site.

7. A method as defined in claim 6 in which said initial incision is formed by the application of pulsed laser energy through said probe.

8. A method as defined in claim 6 and including the additional step of aspirating the ablated tissue through said probe.

9. A method for performing endolaser microsurgery on ocular and like tissues utilizing a laser system and an intraocular probe for delivering the laser energy to the tissues comprising the steps of forming an incision in the conjunctiva surrounding the sclera, advancing the probe through the incision, moving the probe anteriorly beneath the connunctiva to a site remote from the initial incision, and ablating by laser a drainage fistula through the sclera for relieving intraocular pressure, said initial incision in the conjunctiva being made at a site remote from the sclerostomy or sclerostomy site.

10. A method as defined in claim 9 in which said initial incision is formed by the application of pulsed laser energy through said probe.

11. A method as defined in claim 9 and including the additional step of aspirating the ablated tissue through said probe.

12. A method as defined in claim 9 in which said re-securing step includes suturing the displaced conjunctiva at the site of said incision.

* * * * *